(12) United States Patent
Pisano et al.

(10) Patent No.: US 12,059,541 B2
(45) Date of Patent: Aug. 13, 2024

(54) IMPLANTABLE INTERNAL DRAINAGE DEVICE AND SYSTEM FOR EDEMAS

(71) Applicant: CENTRE HOSPITALIER UNIVERSITAIRE VAUDOIS, Lausanne (CH)

(72) Inventors: Marco Pisano, Lausanne (CH); Valentina Triacca, Lausanne (CH)

(73) Assignee: Centre Hospitalier Universitaire Vaudois, Lausanne (CH)

( * ) Notice: Subject to any disclaimer, the term of this patent is extended or adjusted under 35 U.S.C. 154(b) by 906 days.

(21) Appl. No.: 16/620,620

(22) PCT Filed: May 29, 2018

(86) PCT No.: PCT/EP2018/063994
§ 371 (c)(1),
(2) Date: Dec. 9, 2019

(87) PCT Pub. No.: WO2018/224351
PCT Pub. Date: Dec. 13, 2018

(65) Prior Publication Data
US 2020/0197675 A1 Jun. 25, 2020

(30) Foreign Application Priority Data
Jun. 9, 2017 (EP) .................................. 17175319

(51) Int. Cl.
*A61M 27/00* (2006.01)

(52) U.S. Cl.
CPC ...... *A61M 27/002* (2013.01); *A61M 2027/004* (2013.01); *A61M 2205/0288* (2013.01);
(Continued)

(58) Field of Classification Search
CPC ...... A61M 27/002; A61M 27/00; A61M 1/00; A61M 1/0023; A61M 5/14236; A61M 1/962; A61M 25/0026
See application file for complete search history.

(56) References Cited

U.S. PATENT DOCUMENTS 7,491,163 B2 * 2/2009 Viole .................. A61M 1/3653
600/16
2004/0210187 A1 * 10/2004 Zawacki ............. A61M 1/3659
604/523

(Continued)

FOREIGN PATENT DOCUMENTS

CN 203694372 U 7/2014
WO 2015200797 A2 12/2015

OTHER PUBLICATIONS

"Ainla, Alar, The Multifunctional Pipette: A Microfluidic Technology for the Biosciences, Chalmers University of Technology, 2013, p. 12, table 2.1" (Year: 2013).*

(Continued)

*Primary Examiner* — Susan S Su
*Assistant Examiner* — Meagan Ngo
(74) *Attorney, Agent, or Firm* — Weston R. Gould; Dinsmore & Shohl LLP

(57) ABSTRACT

The invention relates to a medical fluid drainage device for drainage of edematous tissues comprising at least one pumping element (1, 23, 33), having an inlet and an outlet, at least one outlet member (2) having at least one lumen, connected directly or indirectly to the outlet of said pumping element and connecting said pumping element to a body cavity or to a vessel or to a subcutaneous area, and at least one inlet member (3) connected to said inlet of said pumping element and providing fluidic connection between said edematous tissue and said pumping element, and characterized in that the inlet member comprises at least two inlet lumens (4, 5,

(Continued)

6) connected in parallel to said inlet of said pumping element, each of said lumens (4, 5, 6) contains at least one fluid access region, wherein each fluid access region (8, 9, 10) being adapted to allow simultaneous edematous fluid entry from distinct regions of said edematous tissue.

16 Claims, 7 Drawing Sheets

(52) U.S. Cl.
    CPC ............. *A61M 2205/103* (2013.01); *A61M 2205/3317* (2013.01); *A61M 2210/1017* (2013.01)

(56) References Cited

U.S. PATENT DOCUMENTS

| 2004/0230179 | A1* | 11/2004 | Shehada | A61B 5/6885 |
| | | | | 600/309 |
| 2005/0069436 | A1* | 3/2005 | Shibasaki | A61M 60/37 |
| | | | | 417/474 |
| 2005/0277804 | A1* | 12/2005 | Pecor | A61M 5/14276 |
| | | | | 600/18 |
| 2012/0245543 | A1* | 9/2012 | Herbert | A61M 39/0247 |
| | | | | 604/327 |
| 2014/0114227 | A1* | 4/2014 | Zamarripa | A61M 27/002 |
| | | | | 604/8 |
| 2015/0305746 | A1* | 10/2015 | Johnson | A61M 1/3655 |
| | | | | 606/153 |
| 2016/0030663 | A1* | 2/2016 | Adaniya | A61M 5/14526 |
| | | | | 604/152 |

OTHER PUBLICATIONS

International Search Report & Written Opinion Issued Aug. 21, 2018.

* cited by examiner

IMPLANTABLE INTERNAL DRAINAGE DEVICE AND SYSTEM FOR EDEMAS

CROSS REFERENCE TO RELATED APPLICATIONS

This application is a U.S. National Stage of international application PCT/EP2018/063994 filed May 29, 2018, which claims priority to European Application No: 17175319.7 filed Jun. 9, 2017, the entire contents of which are incorporated herein by reference.

FIELD OF INVENTION

The present invention generally relates to the draining of physiological fluids and to implantable medical devices for achieving the same. More specifically the present invention relates to pump-based drainage systems, capable of absorbing excess fluid distributed in the subcutaneous space and transporting said fluid to another location such as the peritoneum or another area of the body with functional lymphatic vessels.

BACKGROUND OF THE INVENTION

Edemas are abnormal, excessive accumulation of physiological fluids in a certain area of a living body, more particularly in the connective tissue around the cells which is known as the interstitium. This phenomenon causes severe pain and the swelling of soft tissues due to accumulation of interstitial fluid. The fluid is predominantly water, but protein and cell-rich fluid can accumulate if there is infection or lymphatic obstruction. The swelling is the result of the accumulation of excess fluid under the skin in the spaces within the tissues.

Edema results from increased movement of fluid from the intravascular to the interstitial space, or decreased movement of water from the interstitium into the capillaries or lymphatic vessels. Increased movement of fluid from the intravascular to the interstitial space is due to increased capillary permeability that occurs in infections or as the result of toxin or inflammatory damage to the capillary walls. Edema also results from decreased movement of fluid out of the interstitial space into the capillaries or lymphatic vessels due to lack of adequate plasma oncotic pressure as in nephrotic syndrome, protein-losing enteropathy, or starvation. The lymphatic system is responsible for removing protein and white blood cells (along with some water) from the interstitium. Lymphatic obstruction causes these substances to accumulate in the interstitium.

Furthermore, a variety of different disturbances can induce a condition of edema. These include: an elevated venous hydrostatic pressure which may be caused by thrombosis of a vein or any other venous obstruction; hypoproteinemia with reduced plasma oncotic pressure resulting from either inadequate synthesis or increased loss of albumin; increased osmotic pressure of the interstitial fluid due to abnormal accumulation of sodium in the body because renal excretion of sodium cannot keep pace with the intake; failure of the lymphatics to remove fluid and protein adequately from the interstitial space and an increased capillary permeability to fluids and proteins as occurs in the inflammatory response to tissue injury among others.

Lymphedema is a highly disabling disease that causes swollen body limbs due to the malfunctioning of the lymphatic system. It can be inherited (primary) or it can be a consequence of cancer treatment (secondary). Moreover, it is widespread in developing countries as a result of filariasis, a disease caused by a parasitic worm infection, transmitted by mosquitoes. Lymphedema affects approximately 140 million people worldwide. Although epidemiologic data are controversial, it is estimated that in the United States around 6.8 million people have developed or have high risk of developing lymphedema. The incidence of lymphedema is estimated to be around 20% for people undergoing invasive cancer surgery, or other invasive surgeries as hip and knee replacement, cellulitis removal and coronary-artery bypass graft.

In normal conditions, lymphatic vessels absorb up to 1.5 liters per day of fluid (lymph) from the peripheral tissues and they bring it back to the blood circulation. If the lymphatic system is damaged, its drainage action is impaired, resulting in the subcutaneous accumulation of fluid in the limbs, and consequent local swelling. The accumulation of stagnant lymph causes in time dermatitis, pain, weight gain, fatigue, tissue fibrosis, loss of mobility, localized immunodeficiency and recurrent infections. Depression often occurs due to the aesthetical impairment.

One possible solution for lymphedema could be replacing the function of the damaged lymphatic compartment with an implantable medical system. Implantable medical systems suitable for fluid drainage are known per se. For instance, U.S. Pat. No. 8,157,792 describes a wound drainage system for draining fluid from a wound of a patient. The system includes a system that periodically increases and decreases the application of suction at a drain catheter, together with said drain catheter.

The majority of the edemas are caused by local inflammation and disappear with the resolution of the inflammation. However, a number of edemas become chronic because of a dysfunction of the cardiovascular or of the lymphatic system. In particular, chronic lymphedema is the edema caused by a dysfunction of the lymphatic system, which is not able anymore to drain the lymph from the peripheral subcutaneous space to the blood circulation. It can be inherited or can be caused by a birth defect, though it is frequently caused by cancer treatments and by parasitic infections. Though incurable and progressive, a number of treatments have been investigated to ameliorate symptoms For example, one possible treatment is an implantable system that can drain physiological fluid, in particular lymph, from the peripherical subcutaneous space to the blood circulation, through the peritoneal space or through other functioning lymphatic vessels, in case of chronic lymphedema.

This implantable system comprises implantable pumps that drain fluids from a certain location to other location in a living body and are already available (*Journal of Hepatology*, vol 62, suppl 2, S352). However, such pumping systems are not able to drain fluids from distributed edemas, as they can only drain fluid from a single particular fluid region or cavity (i.e., the peritoneal cavity or the posterior chamber of the eye). It is therefore an object of the invention to provide an implantable system for draining fluids from distributed edemas along a body member.

The document WO2014062679A1 presents a device which may be able to drain lymphatic liquid from a lymphatic vessel. However, the implantation of such device requires a complicated microsurgery, feasible only with specialized instrumentations and particularly trained surgeons.

Further, implantable devices comprising several pierced catheters and pumps mounted in series have been also provided. However, in addition to necessitate implantation of electronic material within the body, this technique is also very limited regarding drainage of several tones together.

In this regard, a primary object of the invention is to solve the above-mentioned problems and more particularly to provide an implantable system for draining fluids which is free of any electronics and capable of draining several zones at the same flow rate.

Accordingly, it is an object of the present invention to provide a system that continuously drains excess liquid from the subcutaneous space to the blood circulation in case of distributed subcutaneous edema, re-establishing fluid homeostasis.

A further object of the invention is to provide a system that drain excess liquids uniformly from the distinct regions of the edematous tissue.

A further object of the invention is to provide a system that does not include electronic components in its implantable parts, so to minimize the risk of malfunctions and failure, as well as minimize the dimension of the pumping system.

A further object of the present invention is to provide a system that can be activated and controlled from outside the living body.

A further object of the present invention is to provide an interface to monitor the correct functioning of the drainage system.

SUMMARY OF THE INVENTION

These objects are achieved thanks to the drainage system and the methods of the present invention.

More particularly, a first aspect of the invention relates to a medical fluid drainage device for drainage of edematous tissues comprising at least one pumping element, having an inlet and an outlet, at least one outlet member having at least one lumen, connected directly or indirectly to the outlet of said pumping element and connecting said pumping element to a body cavity or to a vessel, and at least one inlet member connected to said inlet of said pumping element and providing fluidic connection between said edematous tissue and said pumping element, and characterized in that the inlet member comprises at least two inlet lumens connected in parallel to said inlet of said pumping element, each of said lumens contains at least one fluid access region, wherein each fluid access region being adapted to allow simultaneous edematous fluid entry from distinct regions of said edematous tissue.

According to a preferred embodiment of the present invention, the values of hydraulic resistance of each inlet lumen, in the tract preceding each fluid access region, for the same fluid, have a maximum difference of 30%.

Advantageously each of said inlet lumen is a tube with a circular section presenting a radius R and a hydraulic resistance according to the formula: $Rh_i = k*D_i/R_i^4$, where $Rh_i$ is the hydraulic resistance of the lumen i, k is a constant depending on the fluid flowing in the tube, Di is the length if the lumen i, or the distance between said pumping element inlet and the beginning of the fluid access region of the lumen i, and Ri is the radius of the section of the lumen i.

According to a preferred embodiment of the present invention, the fluid access region includes at least one circular hole with dimensions between 0.1 and 2 mm in diameter, on the lumen wall.

Advantageously said inlet lumens are embedded in one or more implanted, flat-shaped member or patch.

Preferably, said flat-shaped member or patch has a thickness between 0.1 and 3 mm and width between 5 and 100 mm.

According to a preferred embodiment of the present invention, each of said inlet lumen has a rectangular section, presenting a height, a width, and a hydraulic resistance according to the formula: $Rh_i = [k*D_i/(1-0.63h_i/w_i)]*(1/h_i^3 w_i)$, where $Rh_i$ is the hydraulic resistance of the lumen i, k is a constant depending on the fluid flowing in the tube, $D_i$ is the length if the lumen i, or the distance between said pumping element inlet and the beginning of the fluid access region of the lumen i, and $h_i$ and $w_i$ are the height and the width of the section of the lumen i.

Advantageously said pumping element, said outlet members and said inlet members are made of PEEK, PEAK, titanium, silicone or any biocompatible materials.

According to a preferred embodiment of the present invention, the pumping element is a roller pump comprising at least a flexible tube for holding a liquid to be moved, a wall to support the tube having an arc-shaped profile, one or more rollers to compress the tube against the wall in one or more points, a central body holding the rollers and free to rotate around his axis, a permanent magnet, integral with the central body, a case, including an inlet and an outlet for the tube; said pumping element being free of implanted electronic component, electric wires or batteries.

Preferably, the pumping element is a gear pump.

Preferably, the pumping element is a gerotor pump.

Preferably, the outer gear of said gerotor pump is anchored to the pumping element case through bearings balls.

Preferably, the teeth of the inner gear of said gerotor pump are bearing.

Preferably, said gerotor pump comprises at least a case including an inlet and an outlet connector, one inner gear anchored to the case though a bearing, eccentric respect to the case; an outer gear, concentric in respect to the case, having one tooth more respect to the inner gear, and able to rotate in respect to the case; A permanent magnetic disc, diametrically magnetized, integral in part with the inner gear, so that when the magnet rotates around its axis, the inner gear rotates around its axis as well, causing the consequent rotation of the outer gear and performing the pumping action; all said elements assembled so that there is fluidic communication between said inlet connector, the space between said teeth of said gears and said outlet connector.

According to a preferred embodiment of the present invention, said pumping element is an implantable pump.

Advantageously said pumping element is a non-implantable pump, connectable to said inlet and outlet members through percutaneous accesses.

A second aspect of the invention is medical fluid drainage system comprising the medical fluid drainage device of the first aspect of the invention and an external controller adapted to activate and control said pumping element and comprising at least: one or more magnetic field sources for creating a dynamic magnetic field which causes the rotation of the magnetic material in the implantable part and the rotation of the central body and of the rollers as well as a power source able to create and maintain the dynamic magnetic field.

Advantageously said external controller contains at least one Hall sensor, which output is used to determine the distance and the orientation of said permanent magnet in said roller pump relative to said external controller.

According to a preferred embodiment of the present invention, said external controller contains at least four Hall sensors, which output is used to determine the distance and the orientation of said permanent magnet relative to said external controller.

Advantageously, one end of the drainage system may be introduced in a subcutaneous edematous space of a living body, while the other end may be connected to the blood circulation directly (i.e. to a vein or to a lymphatic vessel) or indirectly (i.e through the peritoneum or through the subcutaneous tissue in another area of the body), said ends forming a fluid line.

The draining system may be composed by at least two lumens connected in parallel between them, connected in series to the inlet of a pumping element. The outlet of said pumping element may be connected to an outlet catheter, which may be connected directly or indirectly to the blood stream (i.e., through the peritoneum or through a proximal subcutaneous space with functional lymphatics).

Each one of said lumens may have a fluid access region on its surface, through which the excess fluid can access said lumen. The number of lumens in the drainage system as well as the position of the access regions may depend on the extension and the position of the edema.

In one embodiment of the invention, said lumens may have a closed end. In another embodiment, such lumens may have an open end.

In one embodiment of the invention, said access regions are composed of at least one circular aperture in the lateral surface of the lumen. In another embodiment, said access region may have any other geometrical shape, such as slits or ovals.

In one embodiment of the invention, said lumens are distinct tubular members each having an outer diameter and an inner diameter, connected to the pumping element inlet through a connector. In another embodiment, said lumens are part of the same member, which may have a circular or oval outer section which may change of shape and size along the length of the tubular member, according to the shape and size of the edematous tissue. For example, the section could be oval until a certain length D and circular for the rest of the length L-D. In such embodiment, the lumen may have a circular section.

In a further embodiment, the size and shape of the lumens is dimensioned for offering the same hydraulic resistance (the same pressure drop) on said parallel fluid lines, so that the edematous fluid have the same flow rate in said parallel fluid lines.

In a further embodiment, said lumens have circular sections, and their diameter varies depending on the distance D between the access region and the pumping element inlet, according to the formula: $Rh_i = k \cdot D/R_i^4$, where $Rh_i$ is the hydraulic resistance of the lumen i, k is a constant depending on the fluid flowing in the tube, $D_i$ is the length of the lumen i, or the distance between said pumping element inlet and the beginning of the fluid access region of the lumen i, and $R_i$ is the radius of the section of the lumen i.

In another embodiment of the invention, at least two lumens may be embedded in a flat-shaped member which may be introduced under the skin of the living body in the edematous area. In another embodiment, at least two of said flat shape members are connected in parallel between them, and in series to the pumping element.

Said lumens may be embedded in members made of biocompatible materials as silicone, polyurethane, titanium and PEEK, between others.

In an embodiment of the invention, the system may comprise one pumping element, which may be placed outside the skin of the living body and connected to the inlet and outlet catheters through percutaneous accesses.

In a further embodiment of the invention, the system may comprise one pumping element, which may be placed below the skin of the living body (i.e., inside the living body). In said embodiment, the pumping element may be a roller pump, including a magnetic disc integral with the rotor, able to rotate around its axis. The magnet may rotate in presence of a rotational magnetic field, created by a controller device placed outside the skin of the living body. In a further embodiment, said controller might contain a second magnetic disc, which may be placed in a coaxial position respect to the magnetic disc in the pumping element, and put in rotation around its axis through a rotational motor, directly or through a mechanical gear.

In a further embodiment, the relative position of the said magnetic discs may be controlled by at least one Hall sensor, which computes the direction and intensity of the magnetic field resulting from the interaction of sad magnetic discs.

The above summary of some embodiments is not intended to describe each embodiment of every implementation of the present disclosure. The Figures and Detailed Description, which follow, more particularly exemplify these embodiments.

BRIEF DESCRIPTION OF THE DRAWINGS

Further particular advantages and features of the invention will become more apparent from the following non-limitative description of at least one embodiment of the invention which will refer to the accompanying drawings, wherein.

DETAILED DESCRIPTION OF THE INVENTION

The present disclosure may be understood more readily by reference to the following detailed description presented in connection with the accompanying drawings, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

According to a first aspect of the invention, the implantable drainage system for distributed edemas is designed to be implanted subcutaneously and to drain fluid accumulated in an interstitium of a living host, actively and continuously transporting it, directly or indirectly, to the blood circulation. For instance, said drainage system may be designed to be connected to the peritoneum of a living host. For instance, said drainage system may be designed to transport the fluid from the accumulation interstitial area to another interstitial area, distant from the one to be drained, characterized by functional lymphatics (i.e., sternal area).

Figure 1:
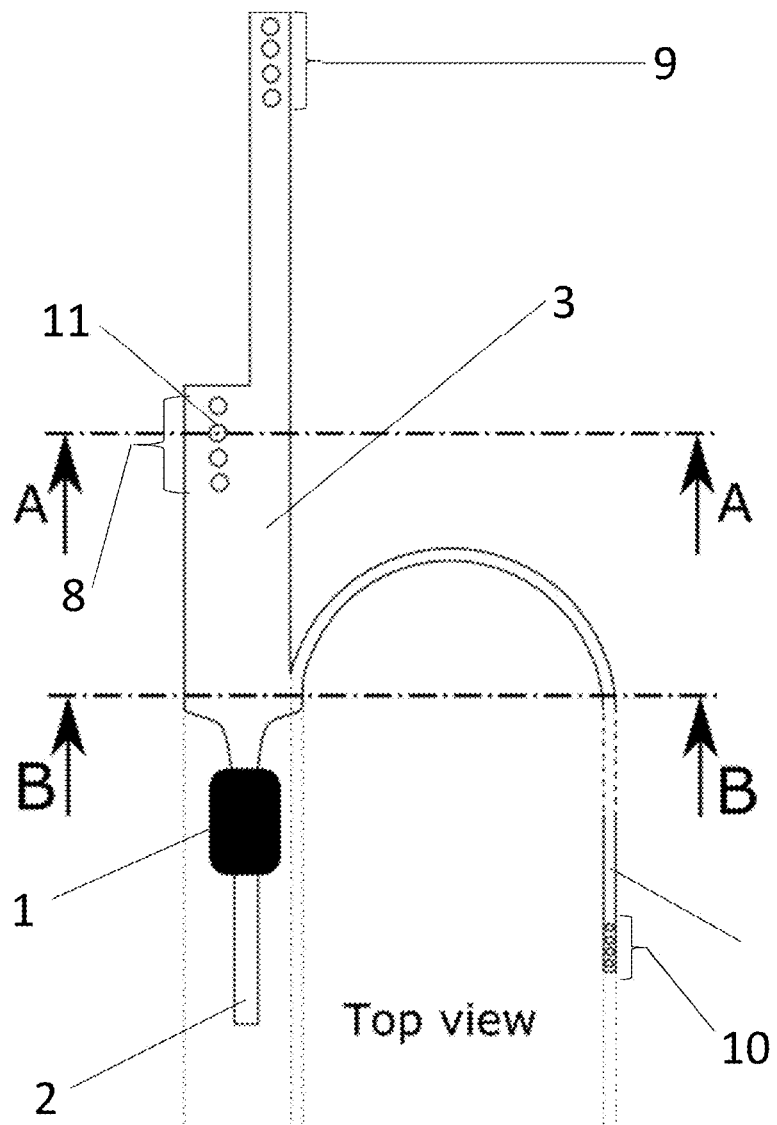
FIG. 1A to 1C show a top view of the medical fluid drainage device of the present invention as well as three sectional views of the device at different positions.
Figure 1:
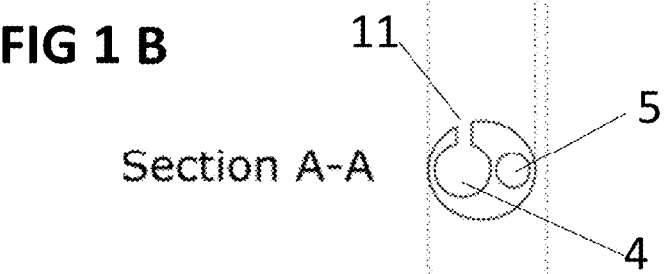
Figure 1:
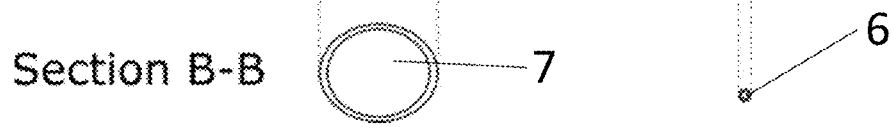

FIGS. 1 A, B and C show the first aspect of the invention which is a transverse view and three section views of the implantable drainage system according to a preferred embodiment of the invention. The system comprises one pumping element 1, one outlet member 2 including a lumen, and one inlet member 3, including three lumens 4, 5, 6 also called inlet lumens. In the present description a lumen shall be considered as any type of tubing element comprising a hollow space and capable of transporting a fluid. The inlet lumens 4, 5, 6 are connected in parallel between them through a common lumen 7. Each of the inlet lumens 4, 5, 6 has a fluid access region 8, 9, 10 in the distal part of said inlet lumen 4, 5, 6, respectively. In this embodiment, for example, the fluid access region 9 allows the entrance of fluid in the lumen 5, which is connected to the lumen 7, which is connected to the pumping element 1, which is connected to the outlet member 2.

In this embodiment, the fluid access regions are composed by four circular holes 11 through the inlet member 3, connecting the lumen 4 with the external fluid. However, the invention is clearly not limited to this embodiment and the fluid access regions may differ from one lumen to another or from one device to another both in number, in shape or even in structure like by adding a filter for regulating the flow rate, or the same for example.

In such embodiment, when the pumping element 1 creates a negative pressure in the lumen 7, such negative pressure will be distributed across the lumens 4, 5, 6, allowing fluid to enter from the access regions 8,9,10 and be transported to the outlet member 2.

The flow rate of the fluid in the lumen 4, 5, 6 depend on the hydraulic resistance offered by said lumens, in the tract between the end of lumen 7, i.e. the proximal end of common lumen 7 with respect to the pump, and the beginning of each lumens, i.e. at the fluid access region 8, 9, 10. If the lumens have a circular section, the hydraulic resistance depends on the length and on the radius of said section to the fourth power ($R^4$).

Having an equal flow rate through the different lumens allows a uniform, thus more efficient, drainage of the edematous tissue. Thus, according to the preferred embodiment of the invention, the diameter of each lumen 4, 5, 6 is determined according to the length of said lumen 4, 5, 6 between the end of the lumen 7 to the first hole of each access region 8, 9, 10, so as to provide a device where each lumen offers the same hydraulic resistance to the edematous fluid.

In particular, the diameter of each lumen can be calculated through the formula:

$$Rh_{4,5,6} = k * D_{4,5,6} / R_{4,5,6}^4$$

where $Rh_{4,5,6}$ is the hydraulic resistance of the lumens 4,5,6, k is a constant depending on the fluid flowing in the tube, $D_{4,5,6}$ is the length if the lumens 4,5,6, or the distance between said pumping element inlet and the beginning of the fluid access region of the lumens 4,5,6, and $R_{4,5,6}$ is the radius of the section of the lumens 4,5,6.

In particular, in order to have an efficient draining, the hydraulic resistance Rh of each lumen must not differ from each other for more than the 30% of their value.

Figure 2:
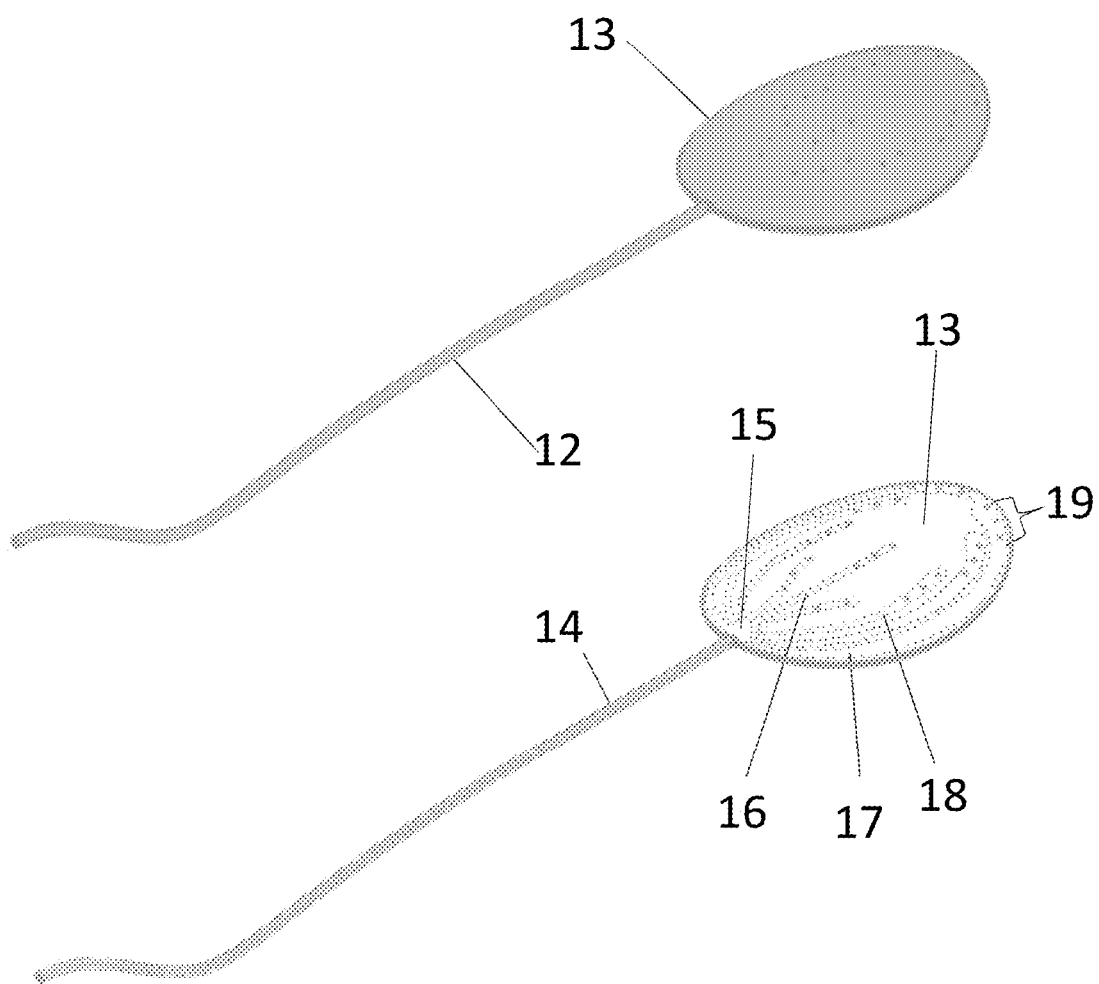
FIG. 2 shows a perspective view of a preferred embodiment of an inlet member for a medical fluid drainage device containing multiple lumens of the present invention.

In a further preferred embodiment of the invention, one of the inlet lumen 4, 5, 6 may not be entirely of tubular shape, but it may have a flat shape or any type of shape, as shown in FIG. 2. In this embodiment, one inlet member is composed of a tubular part 12 and a flat shaped part 13, which may be implanted in the subcutaneous space of a living body, with the tubular part 12 being connected to the input of an implanted pumping element.

The tubular part 12 contains a common lumen 14, which ends with the tip 15, which divides in several inlet lumens as, for example, the lumens 16, 17, 18. Such lumens may have a rectangular section for example. Each lumen has a fluid access region at his terminal part. For instance, lumen 17 has the fluid access region 19 composed by 3 rounded apertures in the upper part of the flat shape member 13.

Thanks to such geometry, when a negative pressure is applied to the tubular part 14, the edematous fluid can enter in the lumens from all the fluid access regions present on the member 13, allowing the drainage as extended as the surface of the flat shape member 13.

Moreover, in order to obtain a similar flow rate in all the lumens in the flat shaped member 13, as for example in the inlet lumens 16, 17, 18, the dimensions (radius) of each lumen can be calculated depending on the length of said lumen, from the common region 15 to the start of each fluid access region. For example, if the lumen 17 has a rectangular section, its height and width can be determined through the formula:

$$Rh_{17} = [k * D_{17} / (1 - 0.63 h_{17}/w_{17})] * (1/h_i^3 w_i),$$

where $Rh_{17}$ is the hydraulic resistance of the lumen 17, k is a constant depending on the fluid flowing in the tube, $D_{17}$ is the length of the lumen 17, as the distance between the common region 15 and the beginning of the fluid access region 19 of the lumen 17, and $h_{17}$ and $w_{17}$ are the height and the width of the section of the lumen 17.

In order to have a similar flow rate in the different lumens, the hydraulic resistance of each lumen must be similar for different lumens, for example $Rh_{17}$ must be similar to $Rh_{16}$ and to $Rh_{18}$. In particular, to have an efficient draining, the hydraulic resistance Rh of each lumen must not differ from each other for more than the 30% of their value.

Figure 3:
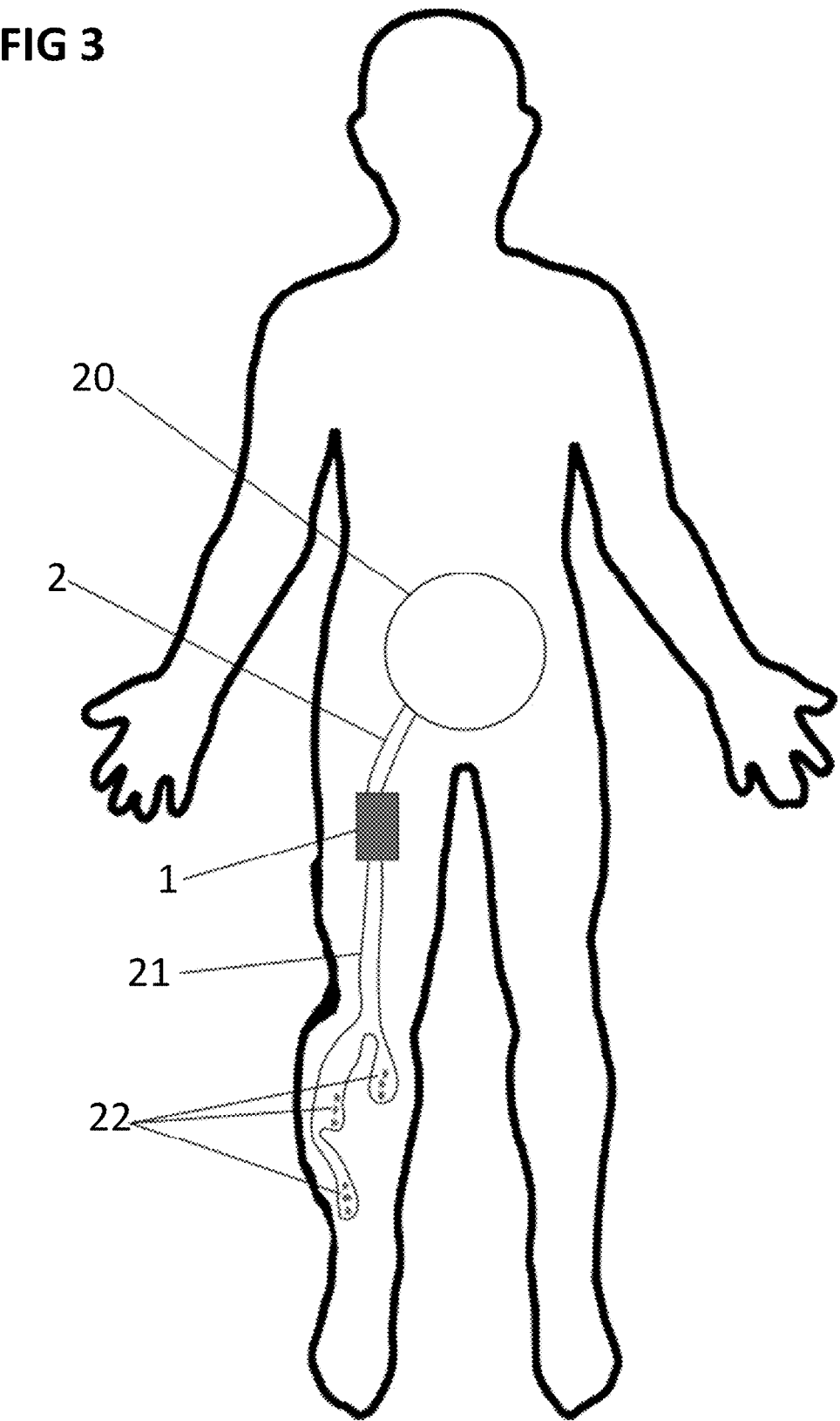
FIG. 3 shows an illustration of an implantation of the medical fluid drainage device of the present invention in which a right leg edema is drained connecting three access regions and 3 inlet lumens to the peritoneum through a pumping element.

The medical fluid drainage system may be configured to drain edematous fluid from a variety of positions in the body. For example, the outlet member 2 may be anchored to the wall of the peritoneum 20 while the system may be positioned in the subcutaneous space of on edematous leg. For instance, in FIG. 3 is shown an example of system configuration including one inlet member 21 comprising three separated lumens and three distinct fluid access regions 22 which drain the edematous fluid and send it the outlet member 2 which then guide it to the peritoneum 20.

The pumping element 1 of the fluid drainage system is the element that creates the necessary negative pressure on the inlet member 3 respect to the outlet member 2, in order to drive the fluid flow in from in the lumens.

Figure 4:
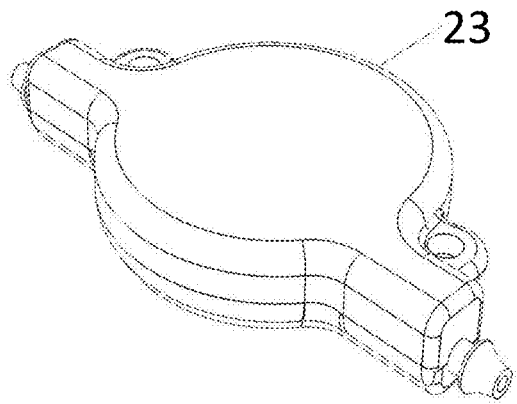
FIG. 4A shows an isometric view of an implantable pumping element according to a first embodiment of the present invention.
FIG. 4B shows an exploded view of the implantable pumping element according to the first embodiment of the present invention.
FIGS. 4C and 4D show a bottom view of the rotating element of the implantable pumping element according to the first embodiment of the present invention.
Figure 4:
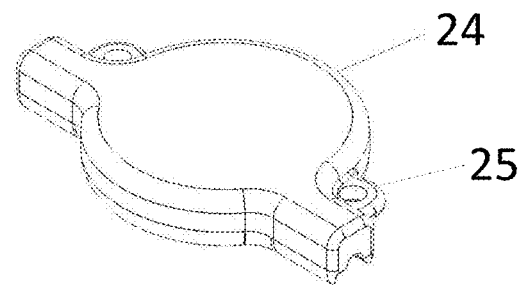
Figure 4:
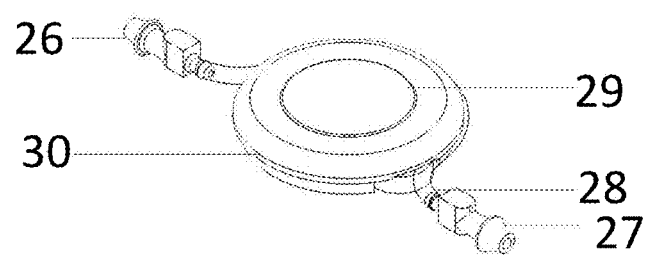
Figure 4:
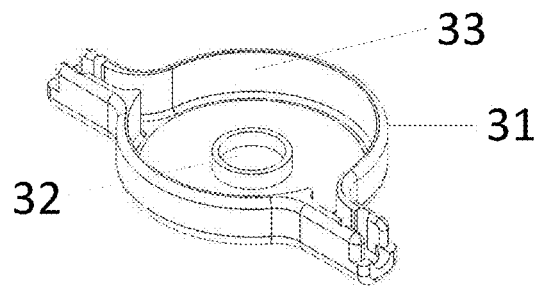
Figure 4:
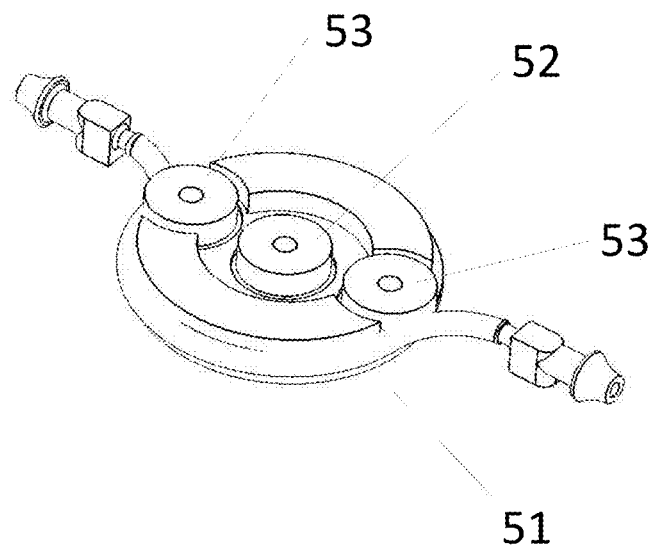
Figure 4:
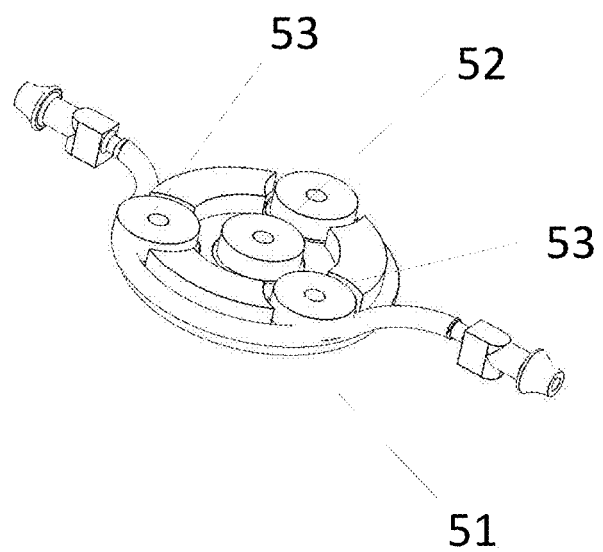

Although several implantable pumping elements are present on the market, a first embodiment is shown in FIG. 4A, which includes an implantable pumping element 23 made in biocompatible material, for example PEEK, PEKK, titanium, silicone, between others. FIG. 4B shows an exploded view of the implantable pumping element 23. It includes an upper shell 24 which comprises two anchoring points 25 to secure the pumping element 23 in position in the subcutaneous space once implanted.

In this embodiment, the pumping element 23 further includes a housed component 51 which comprises an inlet connector 26 and an outlet connector 27, which may be connected to the inlet member 3, or 12, or 21 and to the outlet member 2, respectively. The connectors 26 and 27 are linked together through the flexible member 28. Said flexible member 28 may be in a tubular shape and may be made of a flexible biocompatible material, as for instance, silicone. The flexible member 28 may be in contact with a rotating element 30, which compresses the flexible element 28. The rotating element 30 is solidal with a permanent magnetic disc 29, which may be diametrically magnified, and may be made of a permanent magnetic material, as for instance neodymium. The magnetic disc 29 and/or the rotating element 30 may include a protection layer for the permanent magnet 29 to avoid the degradation of the material of the magnetic disc 29.

The pumping element 23 further includes a bottom shell 31, made of a biocompatible material as PEEK, PEAK, titanium, silicone, between others. The bottom shell 31 includes an anchoring point 32, on which the rotating element 30 may fit so as to be free to rotate. The flexible member 28 may fit between the wall 33 and the rotating element 30. The flexible member may thus be compressed in at least one point between the rotating element 30 and the wall 33. In such way, when the rotating element 30 rotates clockwise, the compression point on flexible member 28 will move clockwise accordingly, creating a negative pressure in the lumen connected to the member 26 respect to the lumen connected to the member 27.

In this embodiment, the rotating element 30 may not rotate unless positioned in a dedicated rotating external magnetic field.

FIGS. 4C and 4D show a bottom view of the central body 51 which clearly shows three of four rollers 52, 53. The central roller 52 is the one disposed on the anchoring point 32 of the bottom shell to allow stable rotation the external rollers 53 are the ones pressing the flexible member 28 thereby creating the negative pressure in the lumen upon rotation. FIG. 4C shows one embodiment of the invention, in which the pumping element contains 2 rollers, which are positioned at a radial angle α between them, with $β-0.5°>α>β-5°$, with β being the angle inside the arc formed by the flexible member 28 on the wall 33, so that it exist one position on the 360° in which none of the rollers 53 is occluding the flexible member 28, creating an "open circuit", which is desirable if the pumping element must be compatible with external compression. In another variation of the invention, presented in FIG. 4D, three rollers 53 are present, placed at equal angle between each other, so that at least one of them is always occluding the flexible member 28, which improves the pump efficiency in case of high pressure loads.

Figure 5:
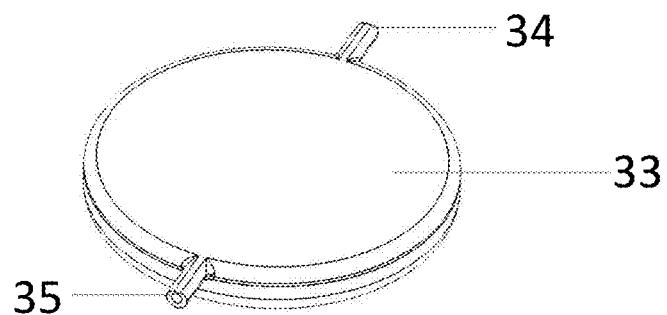
FIG. 5A shows an isometric view of an implantable pumping element according to a second embodiment of the present invention.
FIG. 5B shows an exploded view of the implantable pumping element according to the second embodiment of the present invention.
Figure 5:
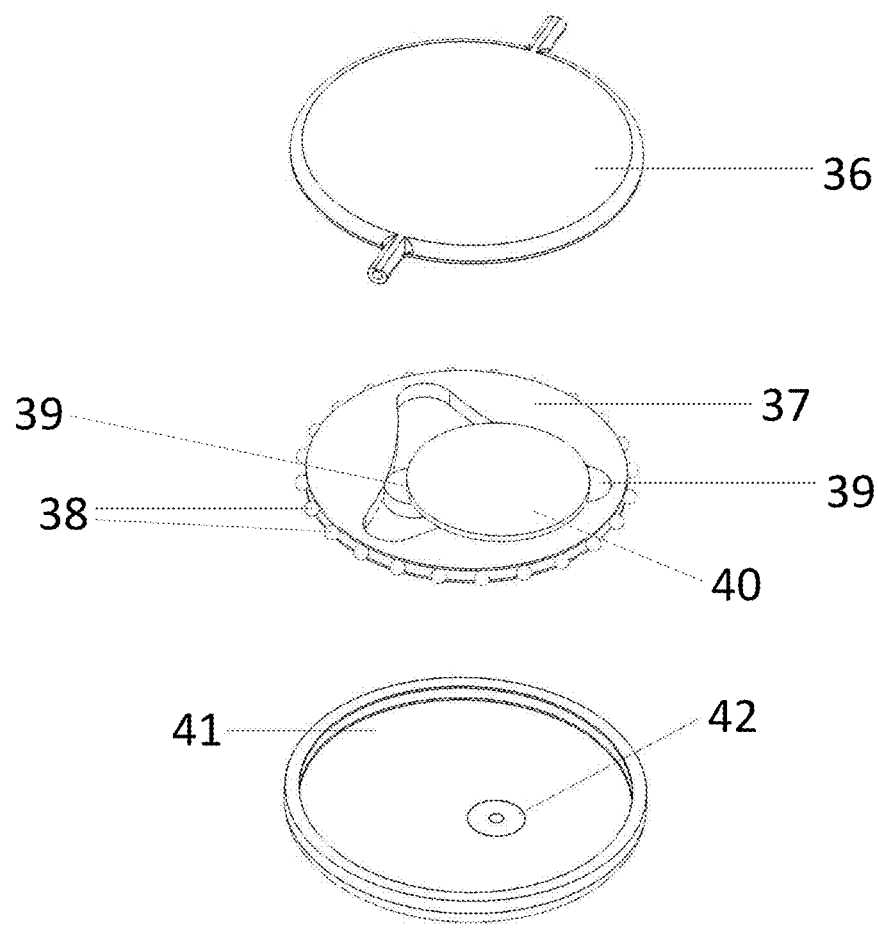

FIGS. 5A and 5B show a second embodiment of the pumping member, which includes an implantable pumping member 33, having an inlet 34 and an outlet 35, integral in part with an upper shell 36 Said implantable pumping member 33 further includes an external 37, concentric with the upper shell 36, able to rotate around its central axis, and having a central hollow part with three concave teeth. The implantable member 33 further includes a central gear, eccentric in respect to the external gear 37, composed by a magnetic disc 40 and two radial bearing 39, each being a tooth of said inner gear. The magnetic disc 40 is solidal with the bearings 39, and can rotate around its axis thanks to the radial gear 42, positioned on a bottom shell 41 and supporting the magnet 40 and the rollers 39. The external gear 37 is supported by a series of bearings 38 placed between the lateral surface of the external gear 37 and the lateral surface of the bottom shell 41, in order to decrease the rotational friction of the external gear 37 and reduce the thickness of the implantable pumping member 33.

Figure 6:
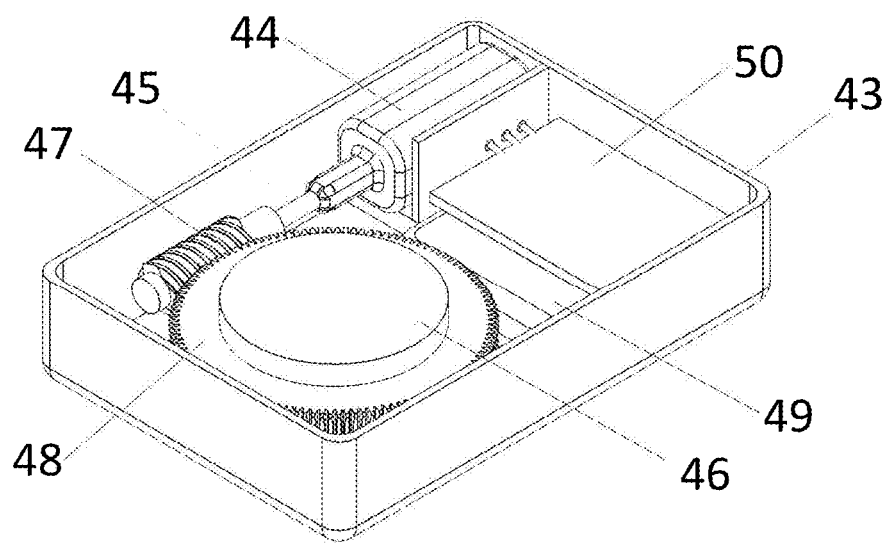
FIG. 6 shows an isometric view of an external controller for the implantable pumping element according to a preferred embodiment of the invention.

FIG. 6 shows an embodiment of a portable external controller creating a rotating magnetic field to drive and control the magnetic disc 29 and therefore the functioning implantable pumping element 23. The external controller may include a case 34, which contains an electromagnetic motor 35. The motor may have a mechanism to transfer the movement of the shaft 36 to a magnetic disc 37. The magnetic disc 37 may be magnetically magnetized and may include a permanent magnetic material as neodymium. In one possible version, shown in FIG. 5, the movement transfer is obtained through a so-called worm wheel, composed by a screw 38 mounted on the shaft 36, and a worm gear 39, integral with the magnetic disc 37. The case 34 may include a battery 40 and an integrated circuit 41.

The external controller may further include one or more Hall sensors, positioned in fixed positions around the magnetic disc, connected to the integrated circuit 41. The output of each hall sensor, combined, may be used to give a feedback on the relative position of the magnetic disc 37 in the external controller with respect to the magnetic disc 29 in the implantable pumping element 23.

While the embodiments have been described in conjunction with a number of embodiments, it is evident that many alternatives, modifications and variations would be or are apparent to those of ordinary skill in the applicable arts. Accordingly, this disclosure is intended to embrace all such alternatives, modifications, equivalents and variations that are within the scope of this disclosure. This is for example particularly the case regarding the fact that the device is primarily contemplated for use in human patients, but the invention will also have veterinary uses or product development purposes in horses, bovines, canines, felines, and other mammals. Further, the applications of the devices and systems discussed above are not limited to certain treatments, while they may include any other condition.

The invention claimed is:

1. A medical fluid drainage device configured to allow drainage of fluid from edematous tissues comprising:
   at least one pumping element having an inlet and an outlet,
   at least one outlet member having at least one lumen, wherein said outlet member is adapted to be connected directly or indirectly to the outlet of said pumping element and wherein said outlet member is adapted to connect said pumping element to a body cavity or to a vessel or to a subcutaneous area, and
   at least one inlet member connected to said inlet of said pumping element and adapted to provide fluidic connection between said edematous tissue and said pumping element, wherein the inlet member comprises at least two inlet lumens having different lengths and running axially in parallel in said inlet member to be connected in parallel to said inlet of said pumping element, each of said inlet lumens contains at least one fluid access region, wherein a first fluid access region comprises a first plurality of holes in a first lateral surface to a first inlet lumen longitudinally offset from a second plurality of holes in a second lateral surface to a second inlet lumen of a second fluid access region, said first and second pluralities of holes being adapted to allow simultaneous edematous fluid entry from distinct regions of said edematous tissue located at different distances from the pumping element, wherein the values of hydraulic resistance of each inlet lumen, in the tract preceding each fluid access region, for the same fluid, have a maximum difference of 30%.

2. The medical fluid drainage device of claim 1, wherein each of said inlet lumen (4, 5, 6) is a tube with a circular section presenting a radius R and a hydraulic resistance according to the formula: $Rh_i = k^* D_i/R_i^4$, where $Rh_i$ is the hydraulic resistance of the lumen i, k is a constant depending on the fluid flowing in the tube, Di is the length if the lumen i, or the distance between said pumping element inlet and the beginning of the fluid access region of the lumen i, and Ri is the radius of the section of the lumen.

3. The medical fluid drainage device of claim 1, wherein said first and second pluralities of holes comprise circular holes with dimensions between 0.1 and 2 mm in diameter, on the lumen wall.

4. The medical fluid drainage device of claim 1, wherein said inlet lumens are embedded in one or more implanted, flat-shaped member (13) or patch.

5. The medical fluid drainage device of claim 4, wherein said flat-shaped member (13) or patch has a thickness between 0.1 and 3 mm and width between 5 and 100 mm.

6. The medical fluid drainage device of claim 1, wherein each of said inlet lumen has a rectangular section, presenting a height, a width, and a hydraulic resistance according to the formula: $Rh_i = [k^* D_i/(1-0.63h_i/w_i)]^*(1/h_i^3 w_i)$, where $Rh_i$ is the hydraulic resistance of the lumen i, k is a constant depending on the fluid flowing in the tube, $D_i$ is the length if the lumen i, or the distance between said pumping element inlet and the beginning of the fluid access region of the lumen i, and $h_i$ and $w_i$ are the height and the width of the section of the lumen.

7. The medical fluid drainage device of claim 1, wherein said pumping element (1, 23, 33), said outlet members (2, 14, 21) and said inlet members (3, 21) are made of PEEK, PEAK, titanium, silicone or any biocompatible materials.

8. The medical fluid drainage device of claim 1, wherein the pumping element (1, 23, 33) is a roller pump comprising at least a flexible tube (28) for holding a liquid to be moved, a wall (33) to support the tube having an arc-shaped profile, one or more rollers (52, 53) to compress the tube against the wall in one or more points, a central body (51) holding the one or more rollers and free to rotate around an axis, a permanent magnet (29), integral with the central body, a case (23), including an inlet and an outlet for the tube; said pumping element being free of implanted electronic components, electric wires or batteries.

9. The medical fluid drainage device of claim 8, wherein said pumping element is an implantable pump.

10. The medical fluid drainage device of claim 8, wherein said pumping element is a non-implantable pump, connectable to said inlet and outlet members through percutaneous accesses.

11. The medical fluid drainage device of claim 1, wherein the pumping element (1, 23, 33) is a gear pump, comprising at least one driving gear integral with a permanent magnetic disc (40) and one driven gear (37), the inlet and the outlet, said pumping element free of implanted electronic components, electric wires or batteries.

12. The medical fluid drainage device of claim 11, wherein said pumping element is an implantable pump.

13. The medical fluid drainage device of claim 11, wherein said pumping element is a non-implantable pump, connectable to said inlet and outlet members through percutaneous accesses.

14. A medical fluid drainage system comprising the medical fluid drainage device of claim 1 and an external controller adapted to activate and control said pumping element and comprising at least: one or more magnetic field sources for creating a dynamic magnetic field which causes rotation of a magnetic material in an implantable part and rotation of a central body and of rollers as well as a power source able to create and maintain the dynamic magnetic field.

15. The medical fluid drainage system of claim 14, wherein said external controller contains at least one Hall sensor, which output is used to determine distance and orientation of a permanent magnet in a roller pump relative to said external controller.

16. The medical fluid drainage device of claim 1, wherein said at least one inlet member comprises a common lumen disposed between said inlet of said pumping element and said inlet lumens, the common lumen in fluidic connection with each of said inlet lumens.

* * * * *